United States Patent [19]

Columbus et al.

[11] Patent Number: 5,032,288

[45] Date of Patent: Jul. 16, 1991

[54] BLOOD COLLECTION METHOD

[75] Inventors: Richard L. Columbus, Rochester; Susan M. Atwood, Newark; Deborah P. Freyler, Rochester; Harvey J. Palmer, Lima, all of N.Y.

[73] Assignee: Eastman Kodak Company, Rochester, N.Y.

[21] Appl. No.: 524,401

[22] Filed: May 16, 1990

Related U.S. Application Data

[63] Continuation-in-part of Ser. No. 442,826, Nov. 29, 1989, abandoned.

[51] Int. Cl.$^5$ .............................................. B01D 21/26
[52] U.S. Cl. .................................. 210/741; 210/781; 210/782; 210/514; 436/177; 494/37; 422/101
[58] Field of Search ............... 210/741, 781, 782, 787, 210/789, 117, 130, 136, 514, 515, 516, 518; 422/101, 102; 436/177; 494/2, 16, 20, 21, 37

[56] References Cited

U.S. PATENT DOCUMENTS

| | | | |
|---|---|---|---|
| 3,849,072 | 11/1974 | Ayres | 210/789 |
| 3,935,113 | 1/1976 | Ayres | 210/516 |
| 3,941,699 | 3/1976 | Ayres | 210/789 |
| 3,945,928 | 3/1976 | Ayres | 210/516 |
| 4,015,775 | 4/1977 | Rohde | 210/789 |
| 4,202,769 | 5/1980 | Greenspan | 210/789 |
| 4,487,700 | 12/1984 | Kanter | 210/789 |
| 4,640,785 | 2/1987 | Carroll et al. | 210/782 |
| 4,708,710 | 11/1987 | Dunn, Jr. | 210/787 |
| 4,788,154 | 11/1988 | Guigan | 210/787 |
| 4,828,716 | 5/1989 | McEwen et al. | 210/789 |

*Primary Examiner*—W. Gary Jones
*Attorney, Agent, or Firm*—Dana M. Schmidt

[57] ABSTRACT

A method of use is disclosed of a device that causes phase separation of whole blood, using much lower centrifugal forces. As a result, leukocytes are separated from blood cells having specific gravities of 1.09 g/ml or higher. The method preferably uses a separation chamber arranged so that its long dimension or axis is parallel, not perpendicular, to the spin axis, and a valve that allows automatic removal of the ligher phase(s).

In one aspect, the method separates a lighter phase from a heavier phase, for example, lymphocytes from whole blood, using a centrifugal force of reduced amount. In another aspect, DNA is extracted readily from the separated lighter phase since it is less likely that the lighter phase will be contaminated by erythrocytes as occurs in conventional separation techniques.

4 Claims, 5 Drawing Sheets

BLOOD COLLECTION METHOD

RELATED APPLICATIONS

This is a continuation-in-part application of U.S. Ser. No. 442,826, filed on Nov. 29, 1989, now abandoned, directed to the method. The device claims of the parent application have been refiled in a continuation-in-part application cofiled herewith.

FIELD OF THE INVENTION

The invention relates to a method of extracting serum from whole blood, and especially the DNA of serum, so that the DNA can be further processed.

BACKGROUND OF THE INVENTION

Blood collection and separating devices have from time immemorial, spun down the whole blood in a container having its long axis oriented parallel, or mostly parallel, to the direction of the centrifugal force. Examples can be seen in, e.g., U.S. Pat. No. 4,012,325. There are several reasons for this orientation. One reason is that when centrifugal forces cease, there is a substantial distance of separation between the heavier red cells and the lighter serum, and at the same time, an interface between the two phases of reduced surface area. As a result, when serum is drawn off, there is less likelihood that the blood cells will redisperse into the lighter serum phase. To further prevent this undesired event, a gel of intermediate specific gravity is often used, to occupy the surface area between the two phases. The spinning of the container about the long axis insures that the depth of the gel that resists remixing after centrifuging, will be substantial.

Stated from an opposite point of view, it has not been considered feasible to spin such containers about one of the shorter axes. The reason is that the distance between the free surface of the separated serum, and its interface with the separated blood cells, becomes very short, with a concommittant large surface area at said interface. This in turn makes blood cell contamination of the serum as it is "poured off" or removed, more likely. Any attempt to use a gel to shore up such a large surface area interface is less likely to succeed, since the gel will have only a short depth to it to resist remixing. (The volume of the gel will be distributed primarily over that large surface area of the interface.)

However, the conventional approach has paid a price for these conclusions. The price is, that Phase separation takes a long time since it has to occur over the longest dimension of the liquid volume. For example, in a blood volume of about 2 mL, using a device similar to that described in the aforesaid '325 patent, the time of separation of the serum from the blood cells is on the order of 5.3 min when spinning at, e.g., 100 g's. It is true, of course, that such separation times are also a function of the centrifugal force applied—the greater the force (e.g., created by higher rpm values), the faster the separation. Thus, typically the forces that are used are well in excess of 1000 g's, as lower forces will cause unacceptable delay in the phase separation. But even at such higher forces, such as 1600 g's, the separation in a 2 mL volume container has not been generally possible in less than 30 sec. Most importantly, however, is a disadvantage that has now been discovered about such centrifugal forces: at the interface between the blood cells and the serum is a layer called the "buffy coat". Among other things, when formed at centrifugal forces in excess of 100 g's, the buffy coat has as an inseparable part thereof, leukocyte cells such as the lymphocyte cells, which contain useful DNA. If those cells could be drawn off, the DNA could be extracted. The problem has been that the phase separation that occurs using conventional containers and centrifuges therefor, insures that those lymphocyte cells are irretrievably mixed with the rest of the buffy coat. It will be readily apparent, therefore, that any attempt to speed up phase separation to less than one minute by drastically boosting the force of spinning, will completely interfere with the retrieval of the lymphocyte cells.

Therefore, prior to this invention there has been a substantial need for a blood phase separation method that allows faster phase separation and/or lower spinning forces, while at the same time somehow solving the high risk of remixing of the phases, noted above.

One approach to dealing with this need would be, of course, the provision of some mechanism that allows for ready withdrawal of the light serum phase from the container, before the centrifugal force is removed. This in turn will aid in retaining the unwanted blood cells in a capture zone of the container, during serum removal, since the centrifugal force will still be applied. In fact, a blood separator device has been proposed that allows serum removal from the container while spinning still occurs—it even occurs by increasing the spinning speed. The device in question is shown, for example, in Japanese Kokai 63/237368. A valve is provided closing off exit passageway from the container, it being spring biased so that it will open only when the centrifugal force is increased beyond the speed used during phase separation, e.g., from 3000 to 5000 rpm. Clearly, in such a device serum can be drawn off with a minimum of risk of red cells remixing with the serum being drawn. However, even in such a device, it was not considered that the "while—centrifuging" serum withdrawal would permit reorienting the device to spin about its short axis. Instead, the device once again insists on the conventional spin orientation wherein the phase separation must occur over the long axis of the container.

Another disadvantage of the device shown in the Japanese publication is that the valve will stay open as long as a high centrifugal force is applied, even in the absence of liquid flow. Clearly, a better construction is one in which the valve automatically closes after all serum is removed. The reasons are that a) failure to do so makes it possible that non serum components, if somehow loosened in the container, can also get out the valve, and b) the still open valve prevents other processing from being accomplished while spinning, on the blood cells remaining in the container. This disadvantage stems from the fact that the valve of this prior device operates only in response to centrifugal force, and NOT in response to the presence of liquid, e.g., serum, which is to be drawn off.

There has been a need, therefore, prior to this invention, for a two phase liquid separation method that will more promptly, and at slower speeds, achieve phase separation and automatic removal of the lighter phase, particularly when processing whole blood.

SUMMARY OF THE INVENTION

I have developed a multi-phase liquid separation method that meets the aforesaid needs. This is achieved preferably by using a device that allows spinning to be done about one of the short dimensions of the liquid compartment rather than the long one and by a more judicious use of valve means allowing removal of the lighter phase during centrifugation. In its preferred form, the valve means are responsive only to pressure from the lighter phase, and not to the centrifugal force. The result is a dramatic reduction in forces used for phase separation, to levels that allow recovery of cellular fractions heretofore lost, without extending the total time of centrifugation unreasonably.

More specifically, in accord with one aspect of the invention there is provided a method of separating a lighter phase from a heavier phase in a two-phase liquid, comprising a) placing the two-phase liquid of a predetermined volume into a first chamber having one void dimension longer than the other orthogonal void dimensions, and b) spinning the chamber about an axis that is generally parallel to the one dimension, at a rate of no greater than 100 g's, and c) drawing off the separated lighter phase into a second chamber adjacent to the first chamber with a valve interposed between the chambers.

In accord with still another aspect of the invention, there is provided a method of extracting DNA for analysis using a shortened procedure, the method comprising the steps of a) in a single centrifuge step, spinning a collection of whole blood in a container at a centrifugal force less than 100 g's for a time sufficient to separate serum and leukocytes from erthrocytes, b) drawing off the serum and leukocytes as a sample into a compartment separate from the erthrocytes, c) heating the sample of separated serum and leukocytes for a time and temperature sufficient to lyse the cells and to congeal the sample, d) extracting DNA that was freed by step c) by adding an aqueous extracting agent to the congealed sample, and e) removing the extracted DNA by separating the extracting agent from the solid matter remaining.

Accordingly it is an advantageous feature of the invention that a phase separation method is provided that gives separations of phases such as in whole blood, at drastically reduced centrifugal forces that still require about the same centrifuging times as conventional devices using forces that are hundreds of g's greater.

It is a related advantageous feature of this invention that DNA is extractable by a shortened procedure.

Other advantageous features will become apparent upon reference to the Description of the Preferred Embodiments, when read in light of the attached drawings.

DESCRIPTION OF THE PREFERRED EMBODIMENTS

The invention is hereinafter described in light of its use in preferred embodiments, wherein blood serum or plasma is the lighter phase of a two-phase liquid, and particularly preferred chambers are described for collecting the serum and/or lymphocytes valved off from the two separated phases, using a ball check valve. In addition, the invention is useful regardless of the type or even presence of a subsequent chamber downstream of the valve, and regardless of the valve construction so long as the method achieves the objectives of the invention.

Figure 1:
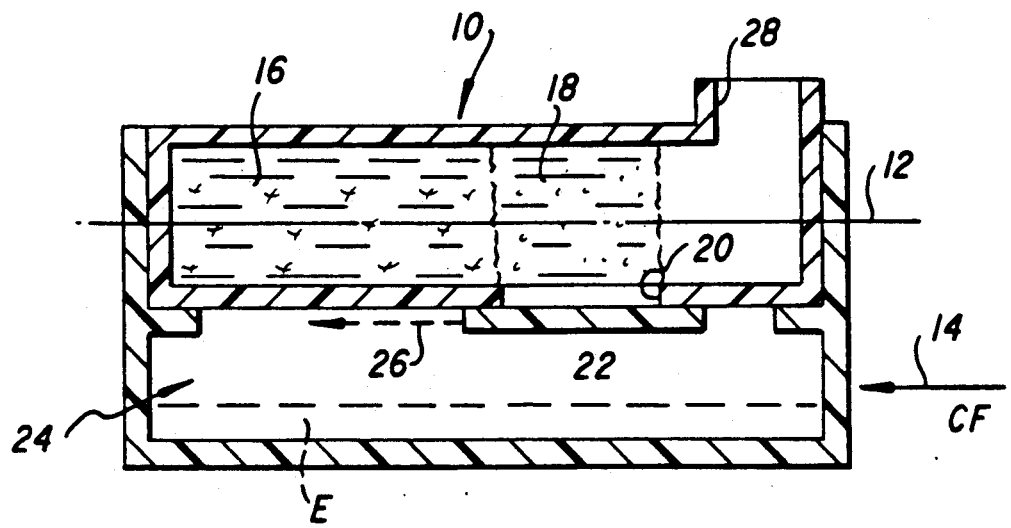
FIG. 1 is an elevational view in section of a serum separation device constructed in accord with the prior art.

Many serum separators of the prior art have conventionally used a container 10, FIG. 1, in which the longitudinal axis 12 of the container is parallel to the direction of centrifugal force CF, arrow 14. As a result, substantial time and force is required to separate the heavier blood cells 16 from the lighter serum 18, into the two fractions shown. In some designs, such as in the Japanese application noted above, a pour-off aperture 20 is provided along with a valve 22, to allow just the serum to flow into a separate-like chamber 24 where it can contact a slide-like test element E, shown in phantom. Valve 22 is constructed to open, arrow 26, only when a centrifugal force (CF) greater than the CF used to separate the two phases, is achieved, the valve moving in that event against a return spring, not shown. This construction has all the attendant disadvantages noted above. In addition, whole blood is added through aperture 28 in a pouring step, that requires operator attention or an intermediate machine step after whole blood is collected in a separate operation via a needle.

Figure 2B:
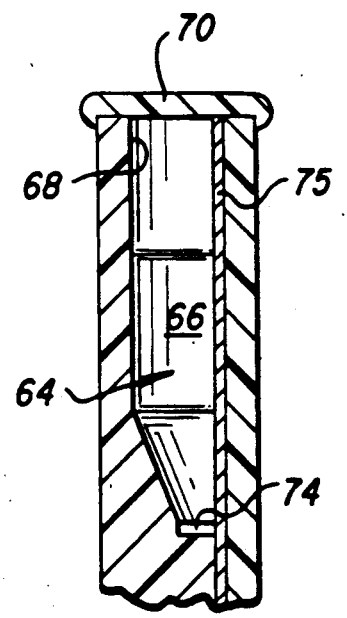
FIG. 2B is a section view taken generally along the line IIB—IIB of FIG. 2A.
Figure 2A:
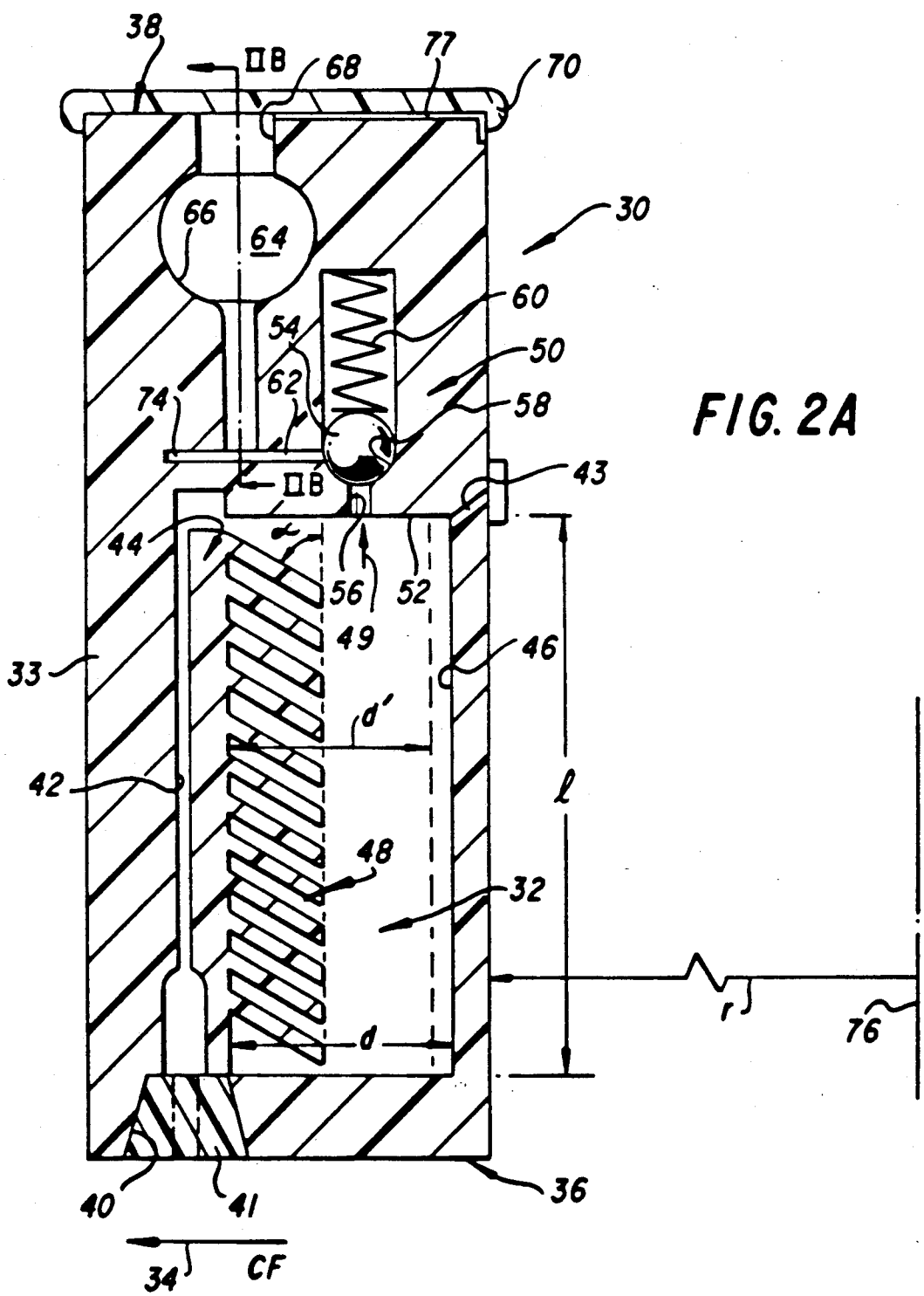
FIG. 2A is an elevational view in section of a serum separation device constructed in accord with this invention.

In accord with the invention, a phase separation device 30, FIG. 2A, for phase separation of at least 2 phases is constructed with a chamber 32 for phase separation that has its long dimension l oriented perpendicular, not parallel, to the direction of centrifugal force CF, arrow 34, and with a specially constructed valve 50. Chamber 32 is defined by a body member 33 having a blood intake end 36 and an opposite, serum removal end 38. Chamber 32 extends from end 36 to delivery passageway 56. End 36 has an intake aperture 40 filled with a conventional septum 41, chamber 32 being either vented at 43 or evacuated due to attachment at 43 to an external vacuum source, to assist in blood intake. Aperture 40 allows entrance of whole blood via passageway 42 to chamber 32. The width "d" of chamber 32 is one of the shorter dimensions, enough blood being drawn in to fill to about the depth d'. Sidewall 44 of chamber 32 is the sidewall against which the heavier blood cells collect, whereas opposite sidewall 46 is adjacent the lighter serum fraction, during centrifugation. Thus, dimensions d and d' extend from the lighter phase into the heavier phase.

Optionally, fixed porous mechanical means, such as baffles 48, can be positioned along wall 44 so as to be disposed in the blood cells. As described in commonly owned U.S. application Ser. No. 325,725 filed on Mar. 20, 1989 entitled, "Phase Separation Container with Fixed Means Preventing Remixing", such means act to retain the heavier phase from remixing when the lighter, serum phase is drawn off. The plates of the baffles are inclined at an angle alpha that resists remixing forces when flow occurs out of chamber 32 in the direction of arrow 49. Preferably, this angle is a value that is between about 30° and about 120°, most preferably about 60°. Preferably, the distance between the individual plates of baffles 48 is between about 0.018 cm and about 0.10 cm, most preferably about 0.025 cm. The thickness of each plate is not critical, so long as a significant number of such plates are present as will create the needed volume between them to collect the blood cells.

Valve 50 is disposed at an end 52 of chamber 32 intermediate ends 36 and 38, positioned to draw off separated, or plasma serum and lymphocytes (discussed hereinafter). Most importantly, valve 50 is constructed to open only in response to a hydraulic head of force, and not to the effects of force CF, regardless of the magnitude of the latter. To this end, valve 50 is preferably a ball check valve with a ball 54 positioned downstream of passageway 56 at chamber end 52. Ball 54 seats against a hemispherical seat 58, and is biased by a spring 60 aligned to act in a direction that is generally perpendicular to the direction of force CF. This alignment tends to ensure that ball 54 will act against spring 60 only in response to forces other than force CF.

A serum or plasma exit passageway 62 is constructed adjacent seat 58, to carry off the liquid when valve 50 opens. Passageway 62 joins a chamber or compartment 64 sized to receive substantially all the liquid that exits in chamber 32 via valve 50. Chamber 64 has a deep well portion 66 designed to collect lymphocytes, and a large opening 68 adapted to allow a pipette access to chamber 64 generally and to well portion 66 in particular. A cover 70 is removably sealed over opening 68 except when access of the pipette or other removal means is desired.

Passageway 62 preferably extends beyond chamber 64 to a trap 74. The function of the trap is to collect the few red blood cells that will gather prior to and during centrifuging, in passageway 56, allowing only desired serum, or plasma and lymphocytes, to pass into chamber 64.

Device 30 can be assembled as two plates, FIG. 2B, using a foil layer 75 to achieve a seal that will allow a vacuum to be drawn using vent 43, as described above.

Such a device 30 can be spun in any convenient centrifuge, not shown, where the long dimension l is generally parallel to the spin axis 76. Preferred spin radii are about 2.5 cm, although a wide variety can be used.

To prevent air entrapment, particularly where such may impede incoming liquid flow, various vents are provided. For example, vent 77 is preferably provided for chamber 64, FIG. 2A. Additionally, not shown, the baffle plates of baffles 48 can have ribs that allow entrapped air to escape.

Figure 3:
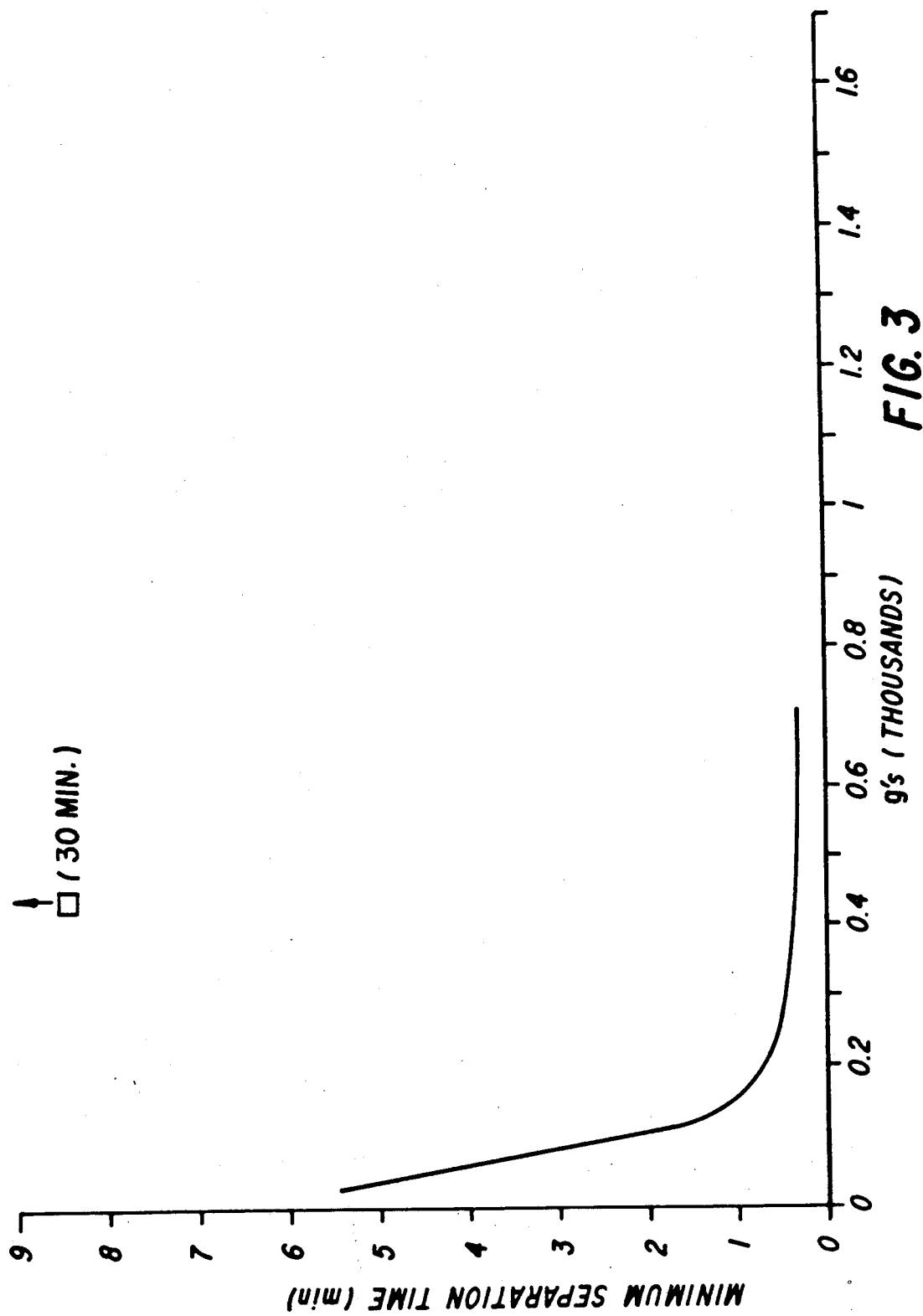
FIG. 3 is a plot of serum separation time vs. centrifugal force, as practiced by the device of this invention.

The method of phase separating, using device 30, will be readily apparent from the preceding discussion. Whole blood is placed into chamber 32 by, e.g., a needle that penetrates septum 41. Device 30 is then spun about axis 76. However, in accord with another aspect of the invention, the speed of rotation that is selected is slow—a speed producing no greater than 400 g's centrifugal force, and most preferably no greater than 30 g's. The reason is that device 30 is capable of achieving phase separation at such forces, using 2 mL of liquid, in less than 2 minutes, and in some cases less than 1 minute, due to the (relatively) short distance (about d'/2) that the blood cells have to traverse to be separated. FIG. 3 illustrates the separation times achievable with the invention, using a 2.5 cm spin radius and a total whole blood volume of 500 μL. As indicated, the serum, or plasma and lymphocytes, is separated in less than 1 minute if the centrifugal force is about 150 g's or greater, there being little separation time enhancement occurring at forces above 400 g's. At the other end, a separation force of only 30 g's will produce complete phase separation in less than 8 minutes, for example, 5.5 minutes. As a comparative example, as described in U.S. Pat. No. 4,818,418 the conditions achieved using a conventional Ficol-Pague/Percoll as an additive are also indicated—a force of 400 g's is effective to achieve separation only after 30 minutes; point FP on FIG. 3.

Whatever centrifugal force that is selected, after serum or plasma separation occurs the lighter phase is then drawn off the stacked liquid in chamber 32, by opening valve 50. This occurs as follows: spring 60 has a spring constant $K_1$ that is pre-selected to resist movement of ball 54 until a certain head of pressure builds up against ball 54. The increased head of pressure occurs by increasing the centrifugal force a factor, for example 50%, above the force used to achieve phase separation. Preferably, the speed of rotation is increased a corresponding amount. Since the serum and blood cells are relatively incompressible against wall 44, the increase in centrifugal force CF translates into an increased force in the direction of arrow 49, which overcomes spring constant $K_1$ of spring 60, and the valve opens. However, this is true only as long as enough serum or plasma remains in chamber 32 to push out aperture 56. When most of the serum or plasma has passed through the valve, the head of pressure occurring even at the increased speed of rotation, drops. As a result, valve 50 closes automatically even at the higher speeds of rotation, unlike the operation of valve 22 in FIG. 1.

Figure 4:
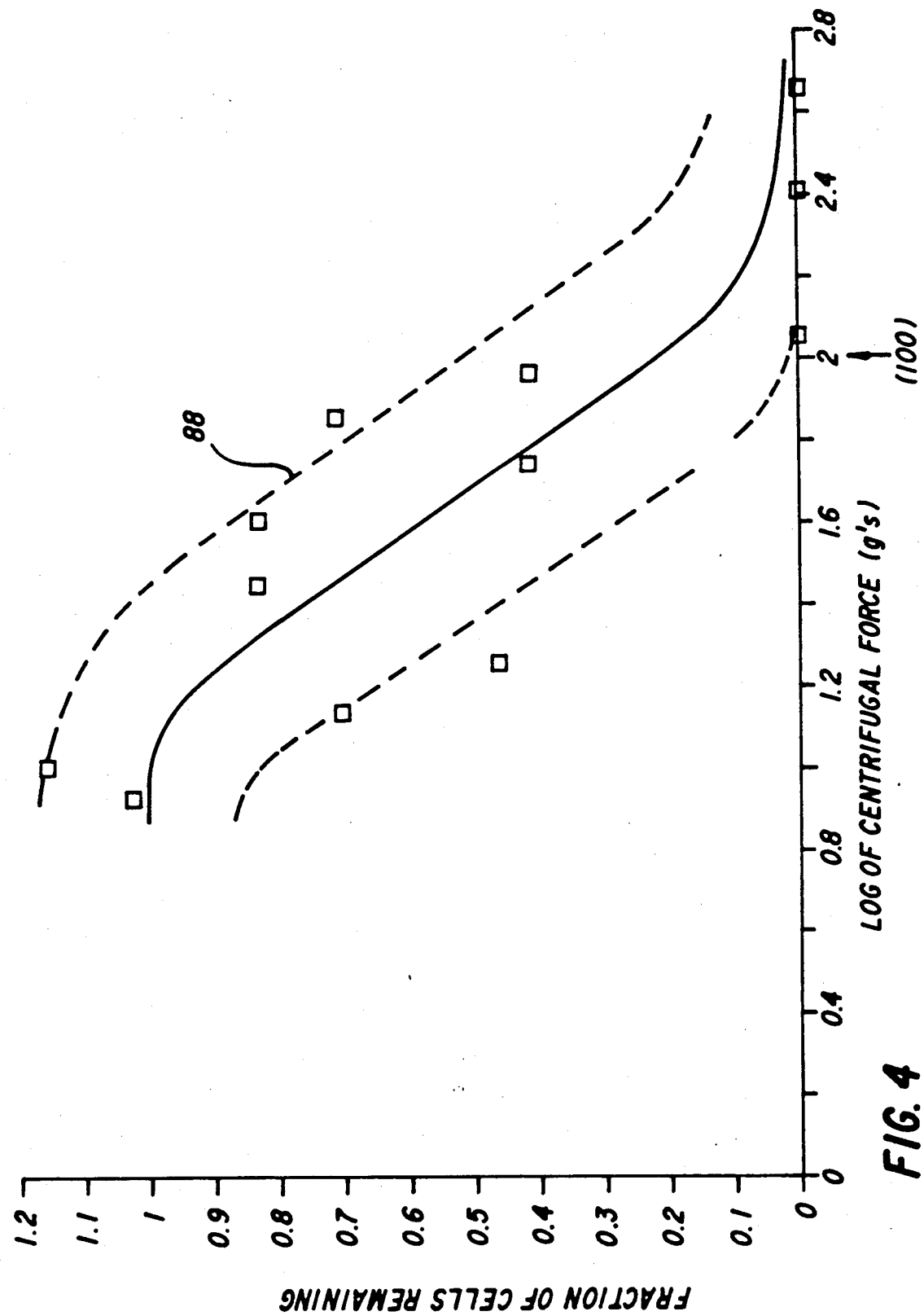
FIG. 4 is a graph of recovered lymphocytes versus the centrifugal force used for phase separation.

FIG. 4 illustrates that in fact this process does produce the separation of lymphocytes, without the necessity of using a chemical phase separation agent common in conventional lymphocyte separation by centrifuging. (If lymphocytes are the desired end-product, then plasma is the lighter phase, rather than serum. Serum is the same as plasma, except that in serum the fibrinogen has been removed, a step considered detrimental to obtaining lymphocytes.) That is, because the centrifugal forces are at a level below about 100 g's, the lymphocytes do not get irretrievably compacted into the buffy coat, as is the case in prior centrifuges that operate at forces above 100 g's.

More specifically, the graph of FIG. 4 was prepared using a device of the type shown in FIG. 2A, in a centrifuge rotor where "r" has the value 2.54 cm (1 inch). Since lymphocytes can all be lost in the red cells if the spin time is allowed to proceed too long before opening valve 50, it is necessary that the process be sampled at varying times for any given centrifugal force $G_i$. Thus, for, e.g., CF=50 g's, many spin times (between 1 and 10 minutes) were examined to determine what optimal time for that CF produces the maximum amount of lymphocytes remaining in the plasma. This is the same as the amount transferred by opening valve 50 by increasing the force CF. The amount of the lymphocytes so remaining in the lighter phase at those optimized times, for each different g force, as a fraction of the total original amount of lymphocytes, was then plotted versus the g forces, expressed as a log to the base 10. FIG. 4 is the result, where a band 88 surrounding the curve has been drawn to "fit" the data. This band symbolizes the uncertainty in the data, where each data point is the mean for the tests. No standard deviation has been determined, however. As noted, the important feature is the recovery of significant fractions of the lymphocytes available. This occurred where the centrifugal force was less than 100 g's.

Once the lymphocytes are recovered, DNA extraction can proceed in accordance with one aspect of the invention. That is, the phase comprising plasma and leukocytes in the second chamber 64 is removed, as with a pipette, and then processed as follows:

1) This phase is heated at a time and temperature that will agglutinate this phase into a pellet. The conditions for this are a temperature of from about 100° C. to 130° C. for from 2 to 20 minutes. This causes a lysing of the leukocytes that frees the DNA. Prior to step #2, the pellet can be optionally preheated with Tris-EDTA buffer.

2) The pellet is then washed with water or another aqueous liquid to extract the DNA from this pellet. Preferably the volume of extracting liquid is such as to increase the volume to a value that is between 200% and 1000% of that of the aliquot volume taken from chamber 64. To assist in this process, the optional step of breaking up the pellet in the presence of the extracting liquid, can be used. Alternatively, the aqueous extracting liquid can be a buffer comprising 0.5 M KCl, 0.1 Molar Tris(hydroxymethyl)aminomethane, 1 mg/ml bone gelatin and 0.1 molar $MgCl_2 \cdot 6H_2O$ at pH of 8.0.

3) The extracting liquid is then separated from the remaining solids of the pellet by conventional methods, for example, decanting or centrifuging, followed by pipetting. Care is taken to not include in the liquid any remaining solids. This completes the DNA extraction.

The steps of this aspect of the method are considerably shorter than the conventional method. The latter features at least 11 steps, wherein centrifuging is done at least three times.

Once the DNA has been extracted, it can be put to a variety of tests. Preferably, in such testing, it is first amplified to make it more readily detectable. Conventional amplification methods are useful, and these include PCR amplification as well as ligase chain reaction (LCR) amplification.

In both of these specific techniques, a thermostable enzyme is used through heat cycling to reproduce the target DNA. In the case of PCR, it is a polymerase enzyme such as TAQ polymerase, that does the reproduction, whereas in LCR, it is a ligase enzyme.

The techniques of PCR amplification can be found in greater detail in, e.g., U.S. Pat. No. 4,683,195. A preferred protocol is as follows:

1) A complete DNA double helix is optionally chemically excised, using an appropriate restriction enzyme(s), to isolate the region of interest.

2) A solution of the isolated nucleic acid portion (here, DNA) and nucleotides is heated to and maintained at 92°-95° C. for a length of time, e.g , no more than about 10 minutes, to denature the two nucleic acid strands; i.e., cause them to unwind and separate and form a template.

3) The solution is then cooled through a 30° C.-60° C. zone, to cause a primer to anneal or "attach" to each of the two template strands. To make sure this happens, the solution is held at an appropriate temperature, such as about 55° C. for about 15 seconds, in an "incubation" zone.

4) The solution is then heated to and held at about 70° C., to cause an extension enzyme, preferably a thermostable polymerase enzyme, to extend the primers bound to the template strands by using the deoxyribonucleotides that are provided for this purpose.

5) The completed new pair of strands is heated to 92°-95° C. again, for about 10-15 seconds, to cause this pair to separate.

6) Steps 3)-5) are then repeated a number of times until the appropriate number of strands are obtained. For example, 70 cycles can be used. The more repetitions, the greater the number of multiples of the nucleic acid (here, DNA) that is produced. Preferably the desired concentration of nucleic acid is reached in a minimum amount of time, wherein each cycle takes less than one minute. However, as much as five minutes can be used for one cycle.

As used herein, the term "primer" refers to an oligonucleotide, whether naturally occurring or synthetically produced, which is capable of acting as a point of initiation of synthesis when placed under conditions in which synthesis of a primer extension product complementary to a nucleic acid strand is induced. Such conditions include the presence of nucleotides (such as the four standard triphosphates) and an deoxyribonucleoside agent for polymerization such as a DNA polymerase, and suitable temperature and pH. Generally, each primer used in this invention will have from 15 to 40 nucleotides, and preferably, it has from 20 to 25 nucleotides.

As for LCR amplification, this also uses probes for a particular target sequence—in fact, those that are adjacent abutting segments when they are bound to the target DNA. The process first causes these probes to bind to the DNA in the abutting relationship, similar to the binding that is done in step 3) above for PCR amplication. Thereafter, the mixture is processed in the presence of ligase at a temperature that will cause the abutted probes to chemically bond end to end, thus replicating a strand of DNA complementary to the targeted strand. There is now created a pair of DNA strands, which is then denatured as in step 5) above for PCR, and the whole cycle repeated to create 4, then 8, etc., copies of the targeted DNA.

Once the targeted DNA has been amplified, or is otherwise present in sufficient quantities, it can be typed using conventional techniques, for example, HLA typing. Such typing procedures are well known, and are described, for example, in Chapter 16 of *PCR Technology* by H. Erlich and T. Bugawan (page 193).

Figure 5:
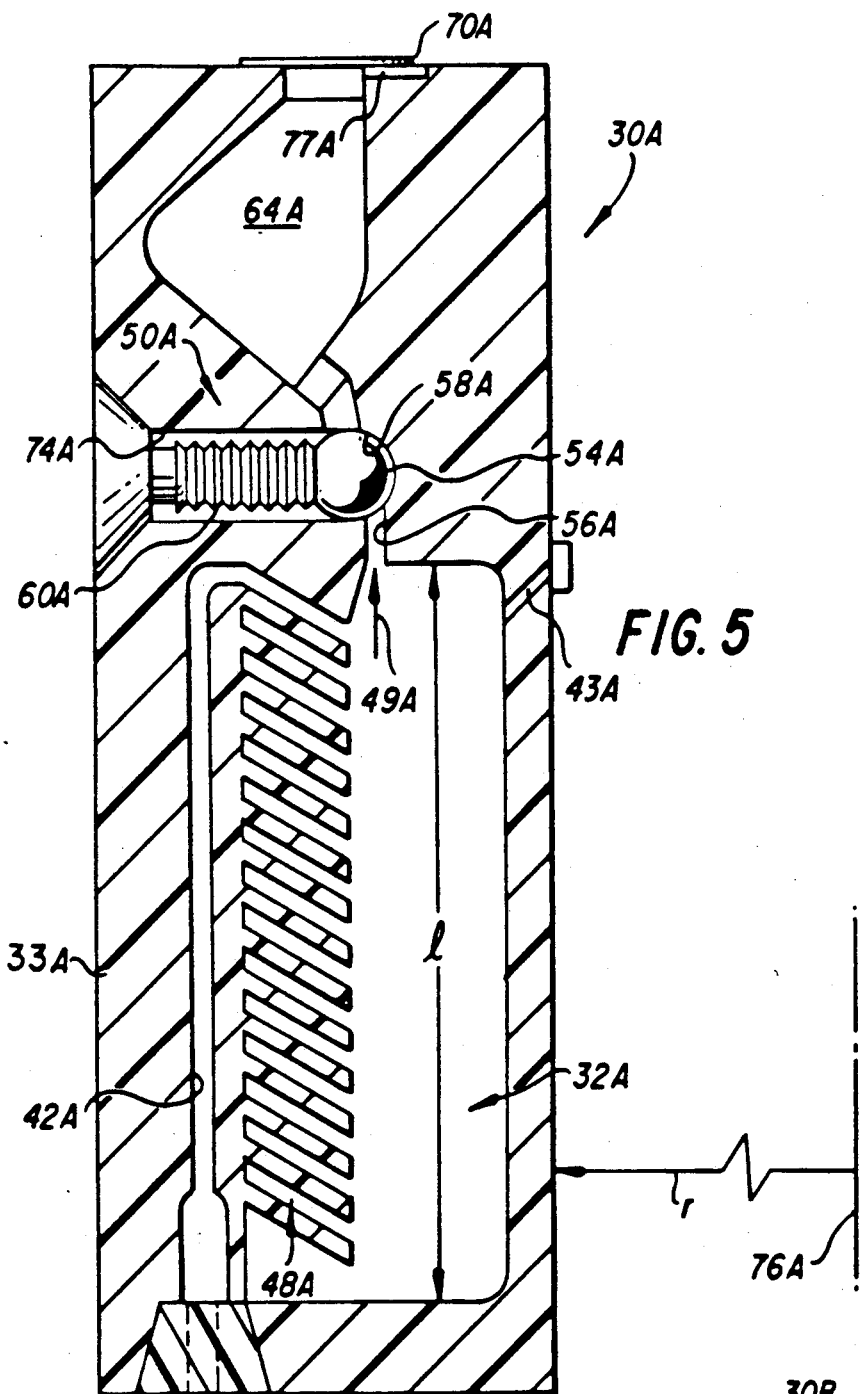
FIG. 5 is an elevational view similar to that of FIG. 2, but of an alternate embodiment.

It is not essential that the valve described above operate on an axis that is neutral to the centrifugal force, as is shown in the alternate embodiment of FIG. 5. Parts similar to those previously described bear the same reference numeral, to which the distinguishing suffix A has been appended.

Thus, device 30A comprises a body 33A having a chamber 32A, passageway 42A supplying blood thereto as before. Baffles 48A can be included to retain the heavier blood cells, and passageway 56A allows removal of the lighter phases such as lymphocytes and plasma, into covered chamber 64A, from chamber 32A, using valve 60A. The long dimension l of chamber 32A is parallel to spin axis 76A. However, in this embodiment spring 60A is oriented to be parallel to the direction of centrifugal force CF. Nevertheless, the spring constant $K_2$ of spring 60A is selected so that ball 54A still opens only in response to a liquid head of pressure, and not in response to the centrifugal force. When ball 54A lifts off seat 58A, the lighter phases pour into chamber 64A. In this embodiment, the volume of passageway 74A that is not filled by spring 60A is just enough to trap any blood cells caught in passageway 56A prior to phase separation.

The careful selection of spring constant $K_2$ of spring 60A is as follows: It is selected so that valve 50A will not open at the first centrifugal speed $CF_1$ used to achieve phase separation. Moreover, it is strong enough to prevent valve opening even in the presence of the higher centrifugal speed $CF_2$ used to create a head of pressure on the valve, in the absence of any liquid pressing on ball 54A. However, because ball 54A has a surface that is included at a non-90° angle to the force of arrow 49A, ball 54A will incur a force parallel to $CF_2$ due to a liquid head of pressure $\Delta P$ generated in the direction of arrow 49A, caused by centrifugal force $CF_2$. (The component of $\Delta P$ that is parallel to $CF_2$ is hereinafter designated $\Delta P_{CF}$.) That is, spring constant $K_2$ is greater than the force generated by $CF_2$ alone, but less than $(CF_2 + \Delta P_{CF})$. When all of the lighter phase liquid has transferred to chamber 64A, there no longer is a liquid head of pressure creating a force $\Delta P_{CF}$, and valve 50A closes automatically, even in the face of a centrifugal force $CF_2$.

The contents of chamber 64A, such as lymphocytes and plasma, are then aspirated out, by removing cover 70A.

Vents 43A and 77A are preferably provided, for the reasons noted for the previous embodiment.

Figure 6A:
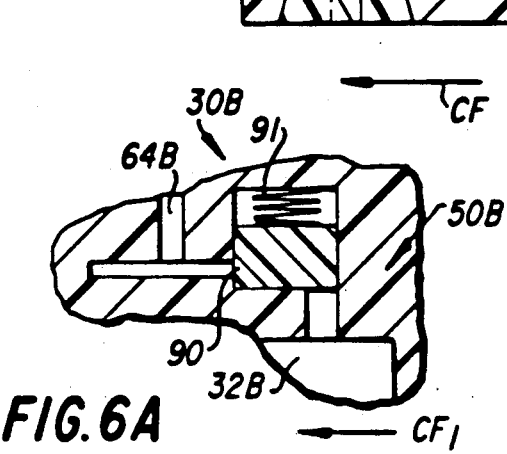
FIGS. 6A and 6B are fragmentary sectional views similar to portions of FIG. 5, but illustrating an alternate embodiment in two positions of use.
Figure 6B:
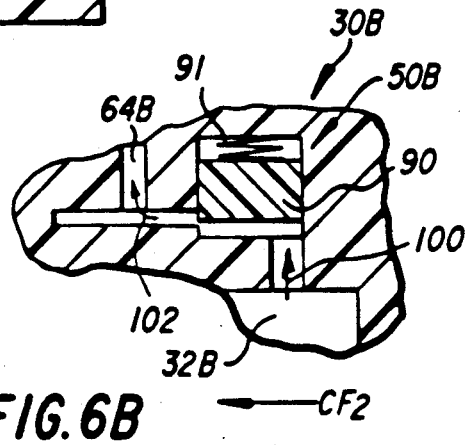

The valve for automatic removal of the lighter phase need not be a ball valve, to respond only to the liquid head of pressure. Any valve can be used, if it is constructed to resist forces other than this head of pressure. Another type is shown in FIGS. 6A and 6B, in which parts similar to those previously described bear the same reference numeral, to which the distinguishing suffix "B" is appended.

Thus, device 30B includes blood collection and separation chambers such as chamber 32B, and a valve 50B that operates only in response to a head of liquid pressure to pass the lighter phase into separate chamber 64B, as in the previous embodiments. However, whereas the previous valves used balls, valve 50B comprises a solid rectangular block 90 backed by a spring 91 of a suitable spring constant selected to deform enough to open the valve, only when centrifugal force is increased from $CF_1$, FIG. 6A, to $CF_2$, FIG. 6B. Flow then proceeds via arrows 100, 102.

The invention has been described in detail with particular reference to preferred embodiments thereof, but it will be understood that variations and modifications can be effected within the spirit and scope of the invention.

What is claimed is:

1. A method of separating a lighter phase from a heavier phase in a two-phase liquid, comprising
   a) placing the two-phase liquid of a predetermined volume into a first chamber having one void dimension longer than the other orthogonal void dimensions,
   b) spinning said chamber about an axis that is generally parallel to said one dimension and offset from said chamber, at a rate of no greater than 400 g's, and
   c) while still spinning said chamber, drawing off the separated lighter phase into a second chamber adjacent to said first chamber with a valve interposed between said chambers.

2. A method as defined in claim 1, wherein said step c) comprises the step of opening said valve solely in response to a predetermined head of liquid pressure generated on said valve by the lighter phase during said spinning step.

3. A method as defined in claim 2, wherein said head of pressure is created by increasing the centrifugal force within said chamber above the force used to achieve phase separation.

4. A method as defined in claim 1, wherein said liquid is whole blood and wherein said separated lighter phase includes lymphocytes.

* * * * *